United States Patent
Blanchard et al.

(10) Patent No.: US 11,229,659 B2
(45) Date of Patent: Jan. 25, 2022

(54) COMPOSITIONS WITH SPECIFIC OLIGOSACCHARIDES TO PREVENT OR TREAT ALLERGIES

(71) Applicant: NESTEC S.A., Vevey (CH)

(72) Inventors: Carine Blanchard, Le Mont-sur-Lausanne (CH); Chiara Nembrini, Oron-la-Ville (CH)

(73) Assignee: Societe des Produits Nestle S.A., Vevey (CH)

( * ) Notice: Subject to any disclaimer, the term of this patent is extended or adjusted under 35 U.S.C. 154(b) by 381 days.

(21) Appl. No.: 16/071,548

(22) PCT Filed: Jan. 26, 2017

(86) PCT No.: PCT/EP2017/051584
§ 371 (c)(1),
(2) Date: Jul. 20, 2018

(87) PCT Pub. No.: WO2017/129644
PCT Pub. Date: Aug. 3, 2017

(65) Prior Publication Data
US 2019/0060334 A1    Feb. 28, 2019

(30) Foreign Application Priority Data
Jan. 26, 2016    (EP) ..................................... 16152743

(51) Int. Cl.
| | |
|---|---|
| *A61K 31/702* | (2006.01) |
| *A23L 33/21* | (2016.01) |
| *A23L 33/135* | (2016.01) |
| *A23L 33/00* | (2016.01) |
| *A61P 37/08* | (2006.01) |
| *A61K 9/00* | (2006.01) |
| *A61K 35/744* | (2015.01) |
| *A61K 35/745* | (2015.01) |
| *A61K 35/747* | (2015.01) |
| *A61K 35/00* | (2006.01) |

(52) U.S. Cl.
CPC .......... *A61K 31/702* (2013.01); *A23L 33/135* (2016.08); *A23L 33/21* (2016.08); *A23L 33/40* (2016.08); *A61K 9/0095* (2013.01); *A61K 35/744* (2013.01); *A61K 35/745* (2013.01); *A61K 35/747* (2013.01); *A61P 37/08* (2018.01); *A23V 2002/00* (2013.01); *A61K 2035/115* (2013.01)

(58) Field of Classification Search
CPC ... A61K 31/702; A61K 35/745; A61K 35/747
See application file for complete search history.

(56) References Cited

U.S. PATENT DOCUMENTS

| | | | |
|---|---|---|---|
| 8,846,642 B2* | 9/2014 | Fichot ....................... | A23L 2/52 514/61 |
| 2011/0064707 A1 | 3/2011 | Rochat et al. | |
| 2012/0171166 A1 | 7/2012 | Chow et al. | |
| 2014/0249103 A1 | 9/2014 | Buck et al. | |
| 2017/0273997 A1* | 9/2017 | Sakwinska .............. | A23L 33/19 |

FOREIGN PATENT DOCUMENTS

| | | | |
|---|---|---|---|
| CH | WO2016026684 | * | 2/2016 |
| EP | 2374362 | | 10/2011 |
| EP | 2455387 | | 5/2012 |
| EP | 2489280 | | 8/2012 |
| EP | 2522232 | | 11/2012 |
| EP | 2526784 | | 11/2012 |
| WO | 2013190530 | | 12/2013 |

OTHER PUBLICATIONS

Thorburn et al. "Evidence that asthma is a developmental origin disease influence by maternal diet and bacterial metabolites" Nature Communications, DOI: 10.1038/ncomms8320, Jun. 23, 2015, 13 pages.
Gibson et al. "Dietary Modulation of the Human Colonic Microbiota: Introducing the Concept of Prebiotics" J. Nutr. 1995, vol. 125, pp. 1401-1412.
Lodge et al. "Breastfeeding and asthma and allergies: a systematic review and meta-analysis" Acta Paediatrica, 2015, vol. 104, pp. 38-53.
Trompette et al. "Gut microbiota metabolism of dietary fiber influences allergic airway disease and hematopoiesis" Nature Medicine, Feb. 2014, vol. 20, No. 2, pp. 159-166.

\* cited by examiner

*Primary Examiner* — Thane Underdahl
(74) *Attorney, Agent, or Firm* — K&L Gates LLP

(57) ABSTRACT

The present invention relates to a nutritional composition comprising an oligosaccharide mixture, said oligosaccharide mixture comprising at least one N-acetylated oligosaccharide, one galacto-oligosaccharide and one sialylated oligosaccharide for use in preventing and/or treating allergy symptoms in an infant or a young child, by increasing SFCA production, in particular colonic acetate, propionate and/or butyrate, in said infant or young children.

11 Claims, 2 Drawing Sheets

COMPOSITIONS WITH SPECIFIC OLIGOSACCHARIDES TO PREVENT OR TREAT ALLERGIES

CROSS REFERENCE TO RELATED APPLICATIONS

The present application is a National Stage of International Application No. PCT/EP2017/051584, filed on Jan. 26, 2017, which claims priority to European Patent Application No. 16152743.7, filed on Jan. 26, 2016, the entire contents of which are being incorporated herein by reference.

FIELD OF THE INVENTION

This invention relates to nutritional compositions such as infant formula, comprising an oligosaccharide mixture which is specifically designed to prevent and/or treat allergies in infants or young children by increasing SFCA production, especially colonic acetate, propionate and butyrate, in such infants or young children. The nutritional compositions of the invention are aimed at allergy prevention and allergy treatment. In the first case, infants or young children are healthy with a normal risk of developing allergy or with a higher risk of developing allergy because one first degree family member have or have had allergy. In the second case, infants or young children are allergic or in needs, hence sick.

BACKGROUND OF THE INVENTION

Allergies are among the most common health problems affecting the life of patients of all age. Allergic diseases are nowadays recognized as an epidemic by the World Health Organization. The prevalence of allergies has been shown to increase in the past decades. Modern life style, especially urban, has been associated with high prevalence and higher severity of allergic manifestations.

Allergic sensitization in childhood, especially in early childhood and especially to food allergens, is critical and of highest interest as development of an "allergic phenotype" or "atopy" has been shown to facilitate subsequent sensitization and allergic reactions to other allergens. Hence allergies in childhood can be the first step of an allergic cascade leading to multiple allergies later in life, a process commonly referred to as "The Atopic March". For example, it has been demonstrated in human cohorts that children with persistent food hypersensitivity early in life have a dramatically increased risk to develop allergic rhinitis (hay fever) or asthma later in childhood (Ostblöm et al 2008). Children with milder forms of food hypersensitivity also have increased risk for development of respiratory allergies but to a lesser degree than children with persistent food hypersensitivity. Therefore, attenuating the severity of food hypersensitivity may be crucial for slowing down the "Atopic March".

In this context the management of allergic episodes and prevention of allergies are, in childhood and infancy, of the highest importance.

The immune system of infants is actively developing all along the few first years of life. Acting on, preventing, avoiding, managing, reducing or modulating the allergic reactions in such young patients can influence their allergic profile short term but also longer term for later in life.

Evidence suggests that infancy may be a critical period in the development of allergies. Mother's milk is recommended for all infants for various reasons. Breastfeeding has been reported to decrease the risk of developing allergies in the offspring Lodge, C J, Breastfeeding and asthma and allergies: a systematic review and meta-analysis, Acta Paediatrica, 2015). However, in some cases breastfeeding is inadequate or unsuccessful for medical reasons or if the mother chooses not to breast feed. Infant formula have been developed for these situations. Fortifiers have also been developed to enrich mother's milk or infant formula with specific ingredients.

Short Chain fatty acids (SCFAs) are especially produced by microbial fermentation of dietary fibres in the colon. SCFA (particularly propionate, acetate) have been shown to protect against allergic airway disease and decrease allergic sensitization (presence of total IgE) (Trompette et al., "*Gut Microbiota metabolism of dietary fiber influences allergic airway disease and hematopoiesis*", Nature Medicine, 2013; Thornburn et al., "*Evidence that asthma is development origin disease influenced by maternal diet and bacterial metabolites*", Nature communications, 2015). Allergic sensitization (presence of total IgE) is a marker for increased risk of developing allergic symptoms, thus the decrease shown in total IgE is to be understood as an indication of efficacy of SFCA in preventing and/or treating allergy beyond airway allergic inflammation, that is, in general.

Increasing SFCA is therefore an attractive target to protect against allergy and allergic symptoms. However, orally administered SCFA can be unpalatable Alternative solutions more appropriate to infants and young children should therefore be developed.

As the composition of human milk becomes better understood, it has been proposed to add prebiotics to infant formula. Various infant formulas supplemented with prebiotics such as mixtures of fructo-oligosaccharides (FOS) and galacto-oligosaccharides (GOS) for example are commercially available. Prebiotics are non-digestible in the sense that they are not broken down and absorbed in the stomach or small intestine and thus pass intact to the colon where they are selectively fermented by the bacteria. The main effect of prebiotics, once fermented, is to selectively promote the growth and metabolic activity of certain species of bacteria recognized as beneficial for the host well-being and health (Roberfroid, M, J. Nutrition, 2007: 37(3): 830S-837S). Beyond the direct effects of prebiotic on the gastro-intestinal flora, prebiotics are known to also have beneficial effects on the host health (such as anticarcinogenic effects, improvement of mineral absorption and effects on metabolite production) that may be due to indirect effects of the prebiotic on the gut microflora.

However, commercially available mixtures approximate only roughly the mixture of oligosaccharides found in human milk. More than 120 different oligosaccharide components have been detected in human milk, some of which have not been detected so far in animal milks (such as bovine milk) at all or have been detected only in small quantities. Some classes of human milk oligosaccharides are present in bovine milk or colostrum only in very small quantities or not at all are sialylated and fucosylated oligosaccharides. As bovine milk contains some oligosaccharides that are structurally identical or similar to those found in human milk, oligosaccharides from bovine milk in sufficient quantities should have prebiotic effect or other beneficial properties associated with human milk oligosaccharides. However until recently, the low concentration of these oligosaccharides in bovine milk (about 20-fold lower than in human milk) has hampered efforts to utilize bovine milk as a source of oligosaccharides for infant formulas.

In addition, few literature exist on the use of bovine milk oligosaccharides for preventing or treating allergy. The patent application WO 2008/116916 describes a nutritional composition for administration to infants which comprises an oligosaccharide mixture consisting of N-acetylated oligosaccharide(s), galacto-oligosaccharide(s) and sialylated oligosaccharide(s) and a probiotic strain to reduce the risk of allergy in babies born by C-section. No effect of a mixture of bovine milk oligosaccharides (BMOs) on the SCFA production was mentioned or suggested in any of these prior documents.

There is clearly a need for developing new and suitable methods to decrease the risk of later in life health conditions related to prevent and/or treat allergy and allergic symptoms in infants and young children.

There is also a need to deliver such health benefits in a manner that is particularly suitable for these young subjects (infants and young children), in a manner that does not involve a classical pharmaceutical intervention as infants or young children are particularly fragile.

There is a need to deliver such health benefits in infants or young children in a manner that does not induce side effects and/or in a manner that is easy to deliver, and well accepted by the parents or health care practitioners.

There is also a need to deliver such benefits in a manner that does keep the cost of such delivery reasonable and affordable by most.

SUMMARY OF THE INVENTION

The present inventors have found that a composition comprising a specific mixture of bovine's milk oligosaccharides (BMOs) can increase colonic SCFA production in an animal model, like propionate, butyrate, valerate and acetate, and especially acetate, butyrate and propionate.

This represents a new clinical situation where prevention and/o treatment of allergy symptoms in an infant or a young child can be targeted in a new way.

Since SCFA are especially known to protect against allergy, such a composition can therefore advantageously be used to prevent and/o treat allergy symptoms in an infant or a young child.

In a particular embodiment, the nutritional composition comprises from 2.5 to 15.0 wt % of the oligosaccharide mixture.

The oligosaccharide mixture comprises at least one N-acetylated oligosaccharide, at least one galacto-oligosaccharide and at least one sialylated oligosaccharide.

It may comprise from 0.1 to 4.0 wt % of the N-acetylated oligosaccharide(s), from 92.0 to 99.5 wt % of the galacto-oligosaccharide(s) and from 0.3 to 4.0 wt % of the sialylated oligosaccharide(s).

The oligosaccharide mixture can be derived from animal milk, such as cow's milk, goat's milk or buffalo's milk.

Abbreviations: Pos ctr=positive control; BMOS=bovine milk oligosaccharides; PDX=polydextrose.

Figure 2:
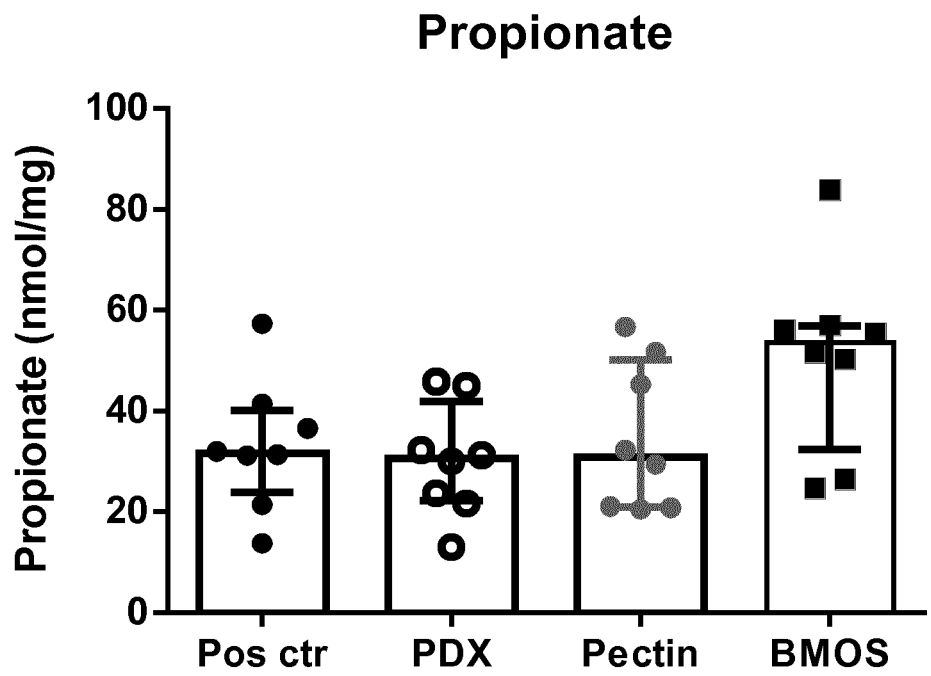

FIG. 2 represents the propionate production from caecum of mice fed with low-fiber diets and with low-fiber diets enriched with 5% of different tested fibers.

Abbreviations: Pos ctr=positive control; BMOS=bovine milk oligosaccharides; PDX=polydextrose.

Figure 3:
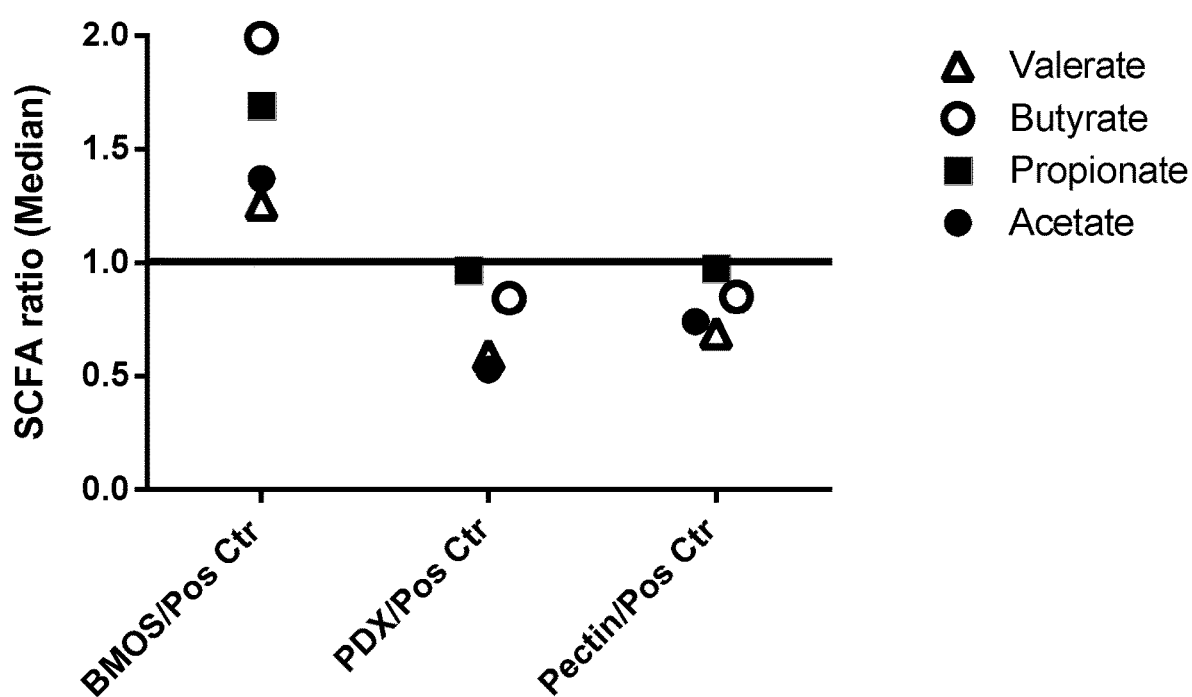

FIG. 3 represents the ratio of the median of each SCFA of fiber-enriched diet divided by the median of the positive control diet.

Abbreviations: Ctrl pos=positive control; BMOS=bovine milk oligosaccharide; PDX=polydextrose.

DETAILED DESCRIPTION OF THE INVENTION

As used herein, the following terms have the following meanings.

The term "infant" means a child under the age of 12 months.

The expression "young child" means a child aged between one and three years, also called toddler.

An "infant or young child born by C-section" means an infant or young child who was delivered by caesarean. It means that the infant or young child was not vaginally delivered.

An "infant or young child vaginally born" means an infant or young child who was vaginally delivered and not delivered by caesarean.

A "preterm" or "premature" means an infant or young child who was not born at term. Generally it refers to an infant or young child born prior 36 weeks of gestation.

The expression "nutritional composition" means a composition which nourishes a subject. This nutritional composition is usually to be taken orally or intravenously. It may include a lipid or fat source, a carbohydrate source and/or a protein source. In a particular embodiment the nutritional composition is a ready-to-drink composition such as a ready-to-drink formula.

In a particular embodiment the composition of the present invention is a hypoallergenic nutritional composition. The expression "hypoallergenic nutritional composition" means a nutritional composition which is unlikely to cause allergic reactions.

In a particular embodiment the nutritional composition of the present invention is a "synthetic nutritional composition". The expression "synthetic nutritional composition" means a mixture obtained by chemical and/or biological means or a mixture comprising components obtained by chemical and/or biological means (including for example purification and separation means), which mixture can be chemically identical to the mixture naturally occurring in mammalian milks or can comprise components which are identical to the components naturally occurring in mammalian milks (i.e. the synthetic nutritional composition is not breast milk).

The expression "infant formula" as used herein refers to a foodstuff intended for particular nutritional use by infants during the first months of life and satisfying by itself the nutritional requirements of this category of person (Article 2(c) of the European Commission Directive 91/321/EEC 2006/141/EC of 22 Dec. 2006 on infant formulae and follow-on formulae). It also refers to a nutritional composition intended for infants and as defined in Codex Alimentarius (Codex STAN 72-1981) and Infant Specialities (incl. Food for Special Medical Purpose). The expression "infant formula" encompasses both "starter infant formula" and "follow-up formula" or "follow-on formula".

A "follow-up formula" or "follow-on formula" is given from the 6th month onwards. It constitutes the principal liquid element in the progressively diversified diet of this category of person.

The expression "baby food" means a foodstuff intended for particular nutritional use by infants or young children during the first years of life.

The expression "infant cereal composition" means a foodstuff intended for particular nutritional use by infants or young children during the first years of life.

The term "fortifier" refers to liquid or solid nutritional compositions suitable for mixing with breast milk or infant formula.

The expression "weaning period" means the period during which the mother's milk is substituted by other food in the diet of an infant or young child.

The expressions "days/weeks/months/years of life", "days/weeks/months/years after birth" and "days/weeks/months/years of birth" can be used interchangeably.

The term "prevention and/or treatment of allergy/allergic response/allergic symptoms/allergic disease" means the prevention and/or the reduction of frequency and/or occurrence and/or severity and/or duration of "allergy" or "allergic response" or "allergic symptoms" or "allergic disease". Occurrence is related to the number of "allergy" or "allergic response" or "allergic symptoms" or "allergic disease". Frequency is related to the number of the same allergy" or "allergic response" or "allergic symptoms" or "allergic disease". This prevention encompasses the reduction of frequency and/or of severity of said "allergy" or "allergic response" or "allergic symptoms" or "allergic disease" later in life. The term "later in life" encompasses the effect after the termination of the intervention.

The expression "later in life" and "in later life" can be used interchangeably. They refer to effects measured in the individual (infant or young child) after the age of some weeks, some months or some years after birth, such as after the age of 6 months after birth, such as after the age of 8 months after birth, such as after the age of 10 months after birth, such as after the age of 1 year after birth, such as after the age of 2 years, preferably after the age of 4 years, more preferably after the age of 5 years, even more preferably after the age of 7 years after birth, or even more, and as a comparison to average observations for subjects of the same age. Preferably it refers to an effect observed after at least 1 year of life, or after at least 2, 5, 7, 10 or 15 years of life. So the expression "later in life" might refer to an observation during infancy, during early childhood, during childhood, during the adolescent period, or during adulthood. Preferably it refers to an observation during childhood, during the adolescent period, or during adulthood. The term "later in life" encompasses the effect after the termination of the intervention.

The expression "health disorder(s)" encompass any health conditions and/or diseases and/or dysfunctions that affect the organism of an individual, including the metabolic ones.

The expression "allergy" or "allergic response" or "allergic symptoms" or "allergic disease" can be used interchangeably. Such terms include, but are not limited to allergic sensitization, food allergy, atopic dermatitis and eczema, wheezing, asthma, allergic rhinitis, rhino-conjunctivitis, eosinophilic esophagitis, hypersensitivity, anaphylaxis, urticaria. Allergy may be developed to different allergens which are all comprised within the scope of this invention; non-limiting examples include proteins derived from food such as cow's milk, eggs, cereals, nuts, or from pollen, from animal dander, from house dust mite.

The term "SCFA" means short chain fatty acid(s).

The expression "increasing SCFA production" means that the amount of systemic and/or SCFA is higher in an individual fed with the nutritional composition according to the present invention (i.e. comprising at least at least one N-acetylated oligosaccharide, at least one galacto-oligosaccharide and at least one sialylated oligosaccharide) in comparison with a standard composition (i.e. a nutritional composition not comprising at least one N-acetylated oligosaccharide, at least one galacto-oligosaccharide and at least one sialylated oligosaccharide) and/or in comparison with a standard composition supplemented with common fibers like polydextrose or pectin. The SCFA may be propionate, butyrate, valerate and/or acetate. In a particular embodiment of the present invention, it is acetate, butyrate and/or propionate. The SCFA production may be measured by techniques known by the skilled person such as by Gas-Liquid Chromatography.

The expression "increasing colonic SCFA production" means that the amount of SCFA, when measured in the colon (or large intestine) or in a part thereof such as the caecum, is higher in an individual fed with the nutritional composition according to the present invention (i.e. comprising at least at least one N-acetylated oligosaccharide, at least one galacto-oligosaccharide and at least one sialylated oligosaccharide) in comparison with a standard composition (i.e. a nutritional composition not comprising at least one N-acetylated oligosaccharide, at least one galacto-oligosaccharide and at least one sialylated oligosaccharide) and/or in comparison with a standard composition supplemented with common fibers like polydextrose or pectin. The SCFA may be propionate, butyrate, valerate and/or acetate. In a particular embodiment of the present invention, it is acetate, butyrate and/or propionate. The SCFA production may be measured by techniques known by the skilled person such as by Gas-Liquid Chromatography.

The "mother's milk" should be understood as the breast milk or the colostrum of the mother.

The term "oligosaccharide" means a carbohydrate having a degree of polymerization (DP) ranging from 2 to 20 inclusive but not including lactose. In some embodiments of the invention, carbohydrate has DP ranging from 3 to 20.

The expressions "at least one N-acetylated oligosaccharide, one galacto-oligosaccharide and one sialylated oligosaccharide" and "at least one N-acetylated oligosaccharide, at least one galacto-oligosaccharide and at least one sialylated oligosaccharide" can be used interchangeably.

The expressions "oligosaccharide(s) mixture" or "mixture of oligosaccharide(s)" can be used interchangeably. The oligosaccharide(s) mixture according to the invention comprises at least one N-acetylated oligosaccharide, at least one galacto-oligosaccharide and at least one sialylated oligosaccharide. The mixture may be made of one or several oligosaccharides of these different types, i.e. one or several N-acetylated oligosaccharide(s), one or several galacto-oligosaccharide(s) and one or several sialylated oligosaccharide(s). In some advantageous embodiments the oligosaccharides of the oligosaccharide mixture are bovine's-derived milk oligosaccharides (or BMOs).

The expression "N-acetylated oligosaccharide" means an oligosaccharide having N-acetyl residue.

The expressions "galacto-oligosaccharide", "galactooligosaccharide" and "GOS" can be used interchangeably. They refer to an oligosaccharide comprising two or more galactose molecules which has no charge and no N-acetyl residue (i.e. they are neutral oligosaccharide).

In a particular embodiment, said two or more galactose molecules are linked by a β-1,2, β-1,3, β-1,4 or β-1,6 linkage.

In another embodiment, "galacto-oligosaccharide" and "GOS" also include oligosaccharides comprising one galactose molecule and one glucose molecule (i.e. disaccharides) which are linked by a β-1,2, β-1,3 or β-1,6 linkage.

The expression "sialylated oligosaccharide" means an oligosaccharide having a sialic acid residue with associated charge.

The terms "prebiotic", "fibre(s)" and "fiber(s)" can be used interchangeably. They refer to non-digestible carbohydrates that beneficially affect the host by selectively stimulating the growth and/or the activity of healthy bacteria such as bifidobacteria in the colon of humans (Gibson G R, Roberfroid M B. *Dietary modulation of the human colonic microbiota: introducing the concept of prebiotics. J Nutr.* 1995; 125:1401-12).

The term "probiotic" means microbial cell preparations or components of microbial cells with a beneficial effect on the health or well-being of the host. (Salminen S, Ouwehand A. Benno Y. et al. "*Probiotics: how should they be defined*" Trends Food Sci. Technol. 1999:10 107-10). The microbial cells are generally bacteria or yeasts.

The term "cfu" should be understood as colony-forming unit.

All percentages are by weight unless otherwise stated.

The nutritional composition of the present invention can be in solid form (e.g. powder) or in liquid form. The amount of the various ingredients (e.g. the oligosaccharides) can be expressed in g/100 g of composition on a dry weight basis when it is in a solid form, e.g. a powder, or as a concentration in g/L of the composition when it refers to a liquid form (this latter also encompasses liquid composition that may be obtained from a powder after reconstitution in a liquid such as milk, water . . . , e.g. a reconstituted infant formula or follow-on/follow-up formula or infant cereal product or any other formulation designed for infant nutrition).

In addition, in the context of the invention, the terms "comprising" or "comprises" do not exclude other possible elements. The composition of the present invention, including the many embodiments described herein, can comprise, consist of, or consist essentially of the essential elements and limitations of the invention described herein, as well as any additional or optional ingredients, components, or limitations described herein or otherwise depending on the needs.

Any reference to prior art documents in this specification is not to be considered an admission that such prior art is widely known or forms part of the common general knowledge in the field.

The invention will now be described in further details. It is noted that the various aspects, features, examples and embodiments described in the present application may be compatible and/or combined together.

A first object of the present invention is therefore a nutritional composition comprising an oligosaccharide mixture, said oligosaccharide mixture comprising at least one N-acetylated oligosaccharide, at least one galacto-oligosaccharide and at least one sialylated oligosaccharide for use in preventing and/or treating allergy symptoms in an infant or a young child, by increasing SFCA production, particularly colonic acetate, propionate and/or butyrate, in said infant or young child.

As illustrated in example 2, the inventors have found that the supplementation of an oligosaccharide mixture according to the present invention increased the SCFA production in an animal model, especially propionate, butyrate, valerate and acetate. Without being bound by theory the inventors of the present invention believe that these particular oligosaccharides act synergistically to surprisingly provide a significant increased SCFA production, in particular colonic acetate, propionate and/or butyrate. Due to the known properties of SCFA, especially butyrate and propionate, such a supplementation could therefore be interestingly used to prevent and/or treat allergy symptoms in infants or young children.

The oligosaccharide mixture of the nutritional composition according to the invention comprises at least one N-acetylated oligosaccharide, at least one galacto-oligosaccharide and at least one sialylated oligosaccharide. As previously mentioned, there may be made of one or several oligosaccharides of these different types, i.e. one or several N-acetylated oligosaccharide(s), one or several galacto-oligosaccharide(s) and one or several sialylated oligosaccharide(s). The oligosaccharide mixture of the nutritional composition of the invention may be prepared from one or more animal milks. The milk may be obtained from any mammal, in particular from cows, goats, buffalos, horses, elephants, camels or sheep.

Alternatively the oligosaccharide mixture may be prepared by purchasing and mixing the individual components.

An N-acetylated oligosaccharide is an oligosaccharide having an N-acetylated residue. Suitable N-acetylated oligosaccharides of the oligosaccharide mixture of the nutritional composition according to the present invention include GalNAcβ1,3Galβ1,4Glc and Galβ1,6GalNAcβ1,3Galβ1,4Glc, but also any mixture thereof. The N-acetylated oligosaccharides may be prepared by the action of glucosaminidase and/or galactoaminidase on N-acetyl-glucose and/or N-acetyl galactose. Equally, N-acetyl-galactosyl transferases and/or N-acetyl-glycosyl transferases may be used for this purpose. The N-acetylated oligosaccharides may also be produced by fermentation technology using respective enzymes (recombinant or natural) and/or microbial fermentation. In the latter case the microbes may either express their natural enzymes and substrates or may be engineered to produce respective substrates and enzymes. Single microbial cultures or mixed cultures may be used. N-acetylated oligosaccharide formation can be initiated by acceptor substrates starting from any degree of polymerization (DP) from DP=1 onwards. Another option is the chemical conversion of keto-hexose (fructose) either free or bound to an oligosaccharide (e.g lactulose) into N-acetyl-hexosamine or an N-acetylhexosamine containing oligosaccharide as described in Wrodnigg, T. M, Dtutz, A. E, Angew. Chem. Int. Ed. 1999: 38: 827-828.

A galacto-oligosaccharide is an oligosaccharide comprising two or more galactose molecules which has no charge and no N-acetyl residue. Suitable galacto-oligosaccharides of the oligosaccharide mixture of the nutritional composition according to the present invention include Galβ1,3Galβ1,4Glc, Galβ1,6Galβ1,4Glc, Galβ1,3Galβ1,3Galβ1,4Glc, Galβ1,6Galβ1,6Galβ1,4Glc, Galβ1,3Galβ1,6Galβ1,4Glc, Galβ1,6Galβ1,3Galβ1,4Glc, Galβ1,6Galβ1,6Galβ1,6Glc, Galβ1,3Galβ1,3Glc, Galβ1,4Galβ1,4Glc and Galβ1,4Galβ1,4Galβ1,4Glc, but also any mixture thereof. Synthesized galacto-oligosaccharides such as Galβ1,6Galβ1,4Glc, Galβ1,6Galβ1,6Galβ1,6Glc, Galβ1,3Galβ1,4Glc, Galβ1,6Galβ1,6Galβ1,4Glc, Galβ1,6Galβ1,3Galβ1,4Glc, Galβ1,3Galβ1,6Galβ1,4Glc, Galβ1,4Galβ1,4Glc and Galβ1,4Galβ1,4Galβ1,4Glc and mixture thereof are commercially available under trademarks Vivinal® and Elix'or®. Other suppliers of oligosaccharides are Dextra Laboratories, Sigma-Aldrich Chemie GmbH and Kyowa Hakko Kogyo Co., Ltd. Alternatively, specific glycotransferases, such as galoctosyltransferases may be used to produce neutral oligosaccharides.

A sialylated oligosaccharide is an oligosaccharide having a sialic acid residue with associated charge. Suitable sialylated oligosaccharides of the oligosaccharide mixture of the nutritional composition according to the present invention include NeuAcβ2,3Galβ1,4Glc and NeuAcβ2,6Galβ1,4Glc, but also any mixture thereof. These sialylated oligosaccharides may be isolated by chromatographic or filtration technology from a natural source such as animal milks. Alternatively, they may also be produced by biotechnology using specific sialyltransferases either by enzyme based fermentation technology (recombinant or natural enzymes) or by microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerization (DP) from DP=1 onwards.

In one aspect of the invention, the nutritional composition comprises the oligosaccharide mixture in an amount from 2.5 to 15 wt %. Alternatively, the nutritional composition comprises the oligosaccharide mixture in an amount from 3 to 15 wt %, or in an amount from 3 to 10 wt %, or in an amount from 3.5 to 9.5 wt % or in an amount from 4 to 9 wt % or in an amount from 4.5 to 8.5 wt %, or in an amount from 5.0 to 7.5 wt % such as 5 wt %.

In some specific embodiments, the nutritional composition may comprise the oligosaccharide mixture in an amount from 0.5 to 3.1 g/100 kcal, or in an amount from 0.6 to 3.1 g/100 kcal, or in an amount from 0.6 to 2.0 g/100 kcal, or in an amount from 0.7 to 2.0 g/100 kcal, or in an amount from 0.8 to 1.8 g/100 kcal, or in an amount from 0.9 to 1.7 g/100 kcal, or in an amount from 1.0 to 1.5 g/100 kcal.

The nutritional composition of the present invention may comprise at least 0.01 wt % of N-acetylated oligosaccharide(s), at least 2.0 wt % of galacto-oligosaccharide(s) and at least 0.02 wt % of sialylated oligosaccharide(s).

In some embodiments, the nutritional composition according to the present invention may comprise at least 0.005 wt % or at least 0.01 wt %, or at least 0.02 wt %, or at least 0.03 wt %, or at least 0.04 wt %, or at least 0.05 wt %, or at least 0.06 wt % of N-acetylated oligosaccharide(s). In some embodiments, it may comprise from 0.005 to 0.06 wt % of N-acetylated oligosaccharide(s) such as from 0.005 to 0.05 wt % or from 0.005 to 0.04 or from 0.005 to 0.03 wt % or from 0.01 to 0.02 wt % of N-acetylated oligosaccharide(s). A particular example is an amount of 0.01 wt % of N-acetylated oligosaccharide(s).

In addition, the nutritional composition may comprise at least 2 wt %, or at least 3 wt %, or at least 4 wt %, or at least 5 wt %, or at least 5.5 wt %, or at least 6 wt % or at least 7 wt % or at least 8 wt % of galacto-oligosaccharide(s). In some embodiments, it may comprise from 4.5 to 8 wt % of galacto-oligosaccharide(s) such as from 4.75 to 6 wt % of galacto-oligosaccharide(s) or from 4.9 to 5 wt % or from 5.5 to 6.5 wt % of galacto-oligosaccharide(s). A particular example is an amount of 4.965 wt % of galacto-oligosaccharide(s).

Finally, the nutritional composition may comprise at least 0.01 wt %, or at least 0.02 wt %, or at least 0.03 wt %, or at least 0.04 wt %, or at least 0.05 wt %, or at least 0.06 wt %, or at least 0.07 wt %, or at least 0.08 wt % or at least 0.09 wt % of sialylated oligosaccharides. In some embodiments, it may comprise from 0.02 to 0.09 wt % of sialylated oligosaccharide(s) such as from 0.02 to 0.07 wt % of sialylated oligosaccharide(s), or from 0.02 to 0.05 wt % of sialylated oligosaccharide(s) or from 0.003 to 0.07 wt % of sialylated oligosaccharide(s). A particular example is an amount of 0.025 wt % of sialylated oligosaccharide(s).

In a particular embodiment, the nutritional composition according to the present invention may comprise from 0.01 to 0.07 wt % of N-acetylated oligosaccharide(s), from 2.0 to 8.0 wt % of galacto-oligosaccharide(s) and from 0.02 to 0.09 wt % of sialylated oligosaccharide(s).

In yet another particular embodiment, the nutritional composition according to the present invention may comprise from 0.01 to 0.03 wt % of N-acetylated oligosaccharide(s), 5.95 wt % galacto-oligosaccharide(s) and from 0.02 to 0.09 wt % of sialylated oligosaccharide(s). In a particular embodiment, the nutritional composition may comprise from 0.0015 to 0.005 g/100 kcal of N-acetylated oligosaccharide(s), from 0.70 to 1.5 g/100 kcal of galacto-oligosaccharide(s) and from 0.0045 to 0.0085 g/100 kcal of sialylated oligosaccharide(s).

In another particular embodiment, the nutritional composition may comprise from 0.0015 to 0.0045 g/100 kcal of N-acetyl-oligosaccharide(s), from 0.74 to 1.2 g/100 kcal of galacto-oligosaccharide(s) and from 0.0045 to 0.0075 g/100 kcal of sialylated oligosaccharide(s).

In a particularly advantageous embodiment, the oligosaccharide mixture of the nutritional composition according to the invention comprises from 0.1 to 4.0 wt % of N-acetylated oligosaccharide(s), from 92.0 to 99.5 wt % of the galacto-oligosaccharide(s) and from 0.3 to 4.0 wt % of the sialylated oligosaccharide(s).

The nutritional composition according to the invention may also contain other types of prebiotic (i.e. different and in addition to the oligosaccharides comprised in the oligosaccharide mixture as defined according to the present invention). Examples of other types of prebiotics include human milk oligosaccharides (HMOs) such as fucosylated oligosaccharides, oligofructose, fructo-oligosaccharides (FOS), inulin, xylooligosaccharides (XOS), polydextrose or any mixture thereof.

Suitable commercial products that can be used in addition to the oligosaccharides comprised in the oligosaccharide mixture to prepare the nutritional compositions according to the invention include combinations of FOS with inulin such as the product sold by BENEO under the trademark Orafti, or polydextrose sold by Tate & Lyle under the trademark STA-LITE®.

The nutritional composition of the present invention can further comprise at least one probiotic (or probiotic strain), such as a probiotic bacterial strain.

The probiotic microorganisms most commonly used are principally bacteria and yeasts of the following genera: *Lactobacillus* spp., *Streptococcus* spp., *Enterococcus* spp., *Bifidobacterium* spp. and *Saccharomyces* spp.

In some particular embodiments, the probiotic is a probiotic bacterial strain. In some specific embodiments, it is particularly Bifidobacteria and/or Lactobacilli.

Suitable probiotic strains include *Lactobacillus acidophilus, Lactobacillus salivarius, Lactobacillus rhamnosus, Lactobacillus paracasei, Lactobacillus casei, Lactobacillus johnsonii, Lactobacillus plantarum, Lactobacillus fermentum, Lactobacillus lactis, Lactobacillus delbrueckii, Lactobacillus helveticus, Lactobacillus bulgari, Lactococcus lactis, Lactococcus diacetylactis, Lactococcus cremoris, Streptococcus salivarius, Streptococcus thermophilus, Bifidobacterium lactis, Bifidobacterium animalis, Bifidobacterium longum, Bifidobacterium breve, Bifidobacterium infantis, Bifidobacterium adolescentis* or any mixture thereof.

Suitable probiotic bacterial strains include *Lactobacillus rhamnosus* ATCC 53103 available from Valio Oy of Finland under the trademark LGG, *Lactobacillus rhamnosus* CGMCC 1.3724, *Lactobacillus paracasei* CNCM I-2116,

*Lactobacillus johnsonii* CNCM I-1225, *Streptococcus salivarius* DSM 13084 sold by BLIS Technologies Limited of New Zealand under the designation KI2, *Bifidobacterium lactis* CNCM 1-3446 sold inter alia by the Christian Hansen company of Denmark under the trademark Bb 12, *Bifidobacterium longum* ATCC BAA-999 sold by Morinaga Milk Industry Co. Ltd. of Japan under the trademark BB536, *Bifidobacterium breve* sold by Danisco under the trademark Bb-03, *Bifidobacterium breve* sold by Morinaga under the trade mark M-16V, *Bifidobacterium infantis* sold by Procter & Gamble Co. under the trademark Bifantis and *Bifidobacterium breve* sold by Institut Rosell (Lallemand) under the trademark R0070.

The nutritional composition according to the invention may contain from 10e3 to 10e12 cfu of probiotic strain, more preferably between 10e7 and 10e12 cfu such as between 10e8 and 10e10 cfu of probiotic strain per g of composition on a dry weight basis.

In one embodiment the probiotics are viable. In another embodiment the probiotics are non-replicating or inactivated. There may be both viable probiotics and inactivated probiotics in some other embodiments.

The nutritional composition of the invention can further comprise at least one phage (bacteriophage) or a mixture of phages, preferably directed against pathogenic Streptococci, *Haemophilus, Moraxella* and Staphylococci.

The nutritional composition according to the invention can be for example an infant formula, a starter infant formula, a follow-on or follow-up formula, a baby food, an infant cereal composition, a fortifier such as a human milk fortifier, or a supplement. In some particular embodiments, the composition of the invention is an infant formula, a fortifier or a supplement that may be intended for the first 4 or 6 months of age. In a preferred embodiment the nutritional composition of the invention is an infant formula.

In some other embodiments the nutritional composition of the present invention is a fortifier. The fortifier can be a breast milk fortifier (e.g. a human milk fortifier) or a formula fortifier such as an infant formula fortifier or a follow-on/follow-up formula fortifier.

When the nutritional composition is a supplement, it can be provided in the form of unit doses.

The nutritional composition of the present invention can be in solid (e.g. powder), liquid or gelatinous form.

The nutritional compositions of the invention, and especially the infant formulas, generally contain a protein source, a carbohydrate source and a lipid source.

The nutritional composition according to the invention generally contains a protein source. The protein can be in an amount of from 1.5 to 3 g per 100 kcal. In some embodiments, especially when the composition is intended for premature infants, the protein amount can be between 2.4 and 4 g/100 kcal or more than 3.6 g/100 kcal. In some other embodiments the protein amount can be below 2.0 g per 100 kcal, e.g. between 1.8 to 2 g/100 kcal, or in an amount below 1.8 g per 100 kcal.

The type of protein is not believed to be critical to the present invention provided that the minimum requirements for essential amino acid content are met and satisfactory growth is ensured. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in any desired proportions.

In some advantageous embodiments the protein source is whey predominant (i.e. more than 50% of proteins are coming from whey proteins, such as 60% or 70%).

The proteins may be intact or hydrolysed or a mixture of intact and hydrolysed proteins. By the term "intact" is meant that the main part of the proteins are intact, i.e. the molecular structure is not altered, for example at least 80% of the proteins are not altered, such as at least 85% of the proteins are not altered, preferably at least 90% of the proteins are not altered, even more preferably at least 95% of the proteins are not altered, such as at least 98% of the proteins are not altered. In a particular embodiment, 100% of the proteins are not altered.

The term "hydrolysed" means in the context of the present invention a protein which has been hydrolysed or broken down into its component amino acids.

The proteins may be either fully or partially hydrolysed. It may be desirable to supply partially hydrolysed proteins (degree of hydrolysis between 2 and 20%), for example for infants or young children believed to be at risk of developing cow's milk allergy. If hydrolysed proteins are required, the hydrolysis process may be carried out as desired and as is known in the art. For example, whey protein hydrolysates may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

In an embodiment of the invention at least 70% of the proteins are hydrolysed, preferably at least 80% of the proteins are hydrolysed, such as at least 85% of the proteins are hydrolysed, even more preferably at least 90% of the proteins are hydrolysed, such as at least 95% of the proteins are hydrolysed, particularly at least 98% of the proteins are hydrolysed. In a particular embodiment, 100% of the proteins are hydrolysed.

In one particular embodiment the proteins of the nutritional composition are hydrolyzed, fully hydrolyzed or partially hydrolyzed. The degree of hydrolysis (DH) of the protein can be between 8 and 40, or between 20 and 60 or between 20 and 80 or more than 10, 20, 40, 60, 80 or 90.

In a particular embodiment the nutritional composition according to the invention is a hypoallergenic composition. In another particular embodiment the composition according to the invention is a hypoallergenic nutritional composition.

The nutritional composition according to the present invention generally contains a carbohydrate source. This is particularly preferable in the case where the nutritional composition of the invention is an infant formula. In this case, any carbohydrate source conventionally found in infant formulae such as lactose, sucrose, saccharose, maltodextrin, starch and mixtures thereof may be used although one of the preferred sources of carbohydrates is lactose.

The nutritional composition according to the present invention generally contains a source of lipids. This is particularly relevant if the nutritional composition of the invention is an infant formula. In this case, the lipid source may be any lipid or fat which is suitable for use in infant formulae. Some suitable fat sources include palm oil, high oleic sunflower oil and high oleic safflower oil. The essential fatty acids linoleic and α-linolenic acid may also be added, as well small amounts of oils containing high quantities of preformed arachidonic acid and docosahexaenoic acid such as fish oils or microbial oils. The fat source may have a ratio of n-6 to n-3 fatty acids of about 5:1 to about 15:1; for example about 8:1 to about 10:1.

The nutritional composition of the invention may also contain all vitamins and minerals understood to be essential in the daily diet and in nutritionally significant amounts. Minimum requirements have been established for certain vitamins and minerals. Examples of minerals, vitamins and other nutrients optionally present in the composition of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population.

If necessary, the nutritional composition of the invention may contain emulsifiers and stabilisers such as soy, lecithin, citric acid esters of mono- and diglycerides, and the like.

The nutritional composition of the invention may also contain other substances which may have a beneficial effect such as lactoferrin, nucleotides, nucleosides, and the like.

The nutritional composition of the invention may also contain carotenoid(s).

The nutritional composition of the invention (e.g. infant formula) may be prepared by blending together the protein source, the carbohydrate source and the fat source in appropriate proportions. Emulsifiers may be added if desired. Vitamins and minerals may be added at this point but are usually added later to avoid thermal degradation. Any lyophilic vitamins, emulsifiers and the like may be dissolved into the fat source prior to blending. Water, preferably water which has been subjected to reverse osmosis, may then be mixed in to form a liquid mixture.

The liquid mixture may then be thermally treated to reduce bacterial loads. For example, the liquid mixture may be rapidly heated to a temperature in the range of about 80° C. to about 110° C. for about 5 seconds to about 5 minutes. This may be carried out by steam injection or by heat exchanger, e.g. a plate heat exchanger.

The liquid mixture may then by cooled to about 60° C. to about 85° C., for example by flash cooling. The liquid mixture may then be homogenized, for example in two stages at about 7 MPa to about 40 MPa in the first stage and about 2 MPa to about 14 MPa in the second stage. The homogenized mixture may then be further cooled to add any heat sensitive components such as vitamins and minerals. The pH and solids content of the homogenized mixture may be conveniently standardized at this point.

The homogenized mixture may be transferred to a suitable drying apparatus, such as spray drier or freeze drier, and may be converted to powder. The powder should have a moisture content of less than about 5% by weight.

The oligosaccharide mixture may be prepared by any suitable manner known in the art and added at different steps during the preparation of the nutritional composition of the present invention. The oligosaccharide mixture can be added directly to the nutritional composition (e.g. infant formula) by dry mixing (i.e. at the blending step). Alternatively, the oligosaccharide mixture can be added in liquid mixture prior to the thermal treatment to reduce the bacterial load. The individual components of the oligosaccharide mixture may also be added separately to the nutritional composition in which case the oligosaccharide mixture is preferably added in the liquid phase immediately prior to drying.

The nutritional composition according to the invention is for use in infants or young children. The infants or young children may be born term or preterm. In a particular embodiment the nutritional composition of the invention is for use in infants or young children that were born preterm. In a particular embodiment the nutritional composition of the invention is for use in preterm infants.

The nutritional composition of the present invention may also be used in an infant or a young child that was born by C-section or that was vaginally delivered.

In some embodiments the nutritional composition according to the invention can be for use before and/or during the weaning period.

In some embodiments the nutritional composition according to the invention is for use in infants or young children at risk of developing allergy. In some embodiments the nutritional composition of the present invention is for use in infants or young children born from allergic women. Indeed, scientific evidence continues to suggest that infants born to allergic mothers have a greater risk of becoming allergic later in life than infants born to mothers who are not allergic.

The nutritional composition can be administered (or given or fed) at an age and for a period that depends on the possibilities and needs.

Since the nutritional composition may be used for prevention purposes (prevention of a later in life health disorder), it can be for example given immediately after birth of the infants. The composition of the invention can also be given during the first week of life of the infant, or during the first 2 weeks of life, or during the first 3 weeks of life, or during the first month of life, or during the first 2 months of life, or during the first 3 months of life, or during the first 4 months of life, or during the first 6 months of life, or during the first 8 months of life, or during the first months of life, or during the first year of life, or during the first two years of life or even more. In some particularly advantageous embodiments of the invention, the nutritional composition is given (or administered) to an infant within the first 4 or 6 months of birth of said infant.

In some other embodiments, the nutritional composition of the invention is given few days (e.g. 1, 2, 3, 5, 10, 15, 20 . . . ), or few weeks (e.g. 1, 2, 3, 4, 5, 6, 7, 8, 9, 10 . . . ), or few months (e.g. 1, 2, 3, 4, 5, 6, 7, 8, 9, 10 . . . ) after birth. This may be especially the case when the infant is premature, but not necessarily.

In one embodiment the composition of the invention is given to the infant or young child as a supplementary composition to the mother's milk. In some embodiments the infant or young child receives the mother's milk during at least the first 2 weeks, first 1, 2, 4, or 6 months. In one embodiment the nutritional composition of the invention is given to the infant or young child after such period of mother's nutrition, or is given together with such period of mother's milk nutrition. In another embodiment the composition is given to the infant or young child as the sole or primary nutritional composition during at least one period of time, e.g. after the $1^{st}$, $2^{nd}$ or $4^{th}$ month of life, during at least 1, 2, 4 or 6 months.

In one embodiment the nutritional composition of the invention is a complete nutritional composition (fulfilling all or most of the nutritional needs of the subject). In another embodiment the nutrition composition is a supplement or a fortifier intended for example to supplement human milk or to supplement an infant formula or a follow-on formula.

The oligosaccharide mixture present in the nutritional composition of the invention may be prepared from one or more animal milks. The milk can be obtained from any mammal, in particular from cows, goats, buffalos, horses, elephants, camels or sheep. In a specific embodiment, the oligosaccharides of the oligosaccharide mixture are bovine's milk oligosaccharides and can be obtained from cows, goats or buffalos' milk. In an advantageous embodiment, the oligosaccharides are obtained from cow's milk. WO2006087391 and WO2012160080 provide some examples of production of a BMOs mixture.

The present inventors have found that the BMOs intervention in an animal model increased its colonic SCFA production, especially the caecum SCFA production and particularly butyrate and propionate. Since these SCFA have been shown to protect against allergy, the nutritional composition according to the present invention would therefore be useful in preventing and/or treating allergy symptoms in an infant or a young child, by increasing SFCA, particularly colonic SCFA, production in said infant or young children.

There may be one or several SCFA which production is increased. The SCFA may be propionate, butyrate, valerate and/or acetate. In a particular embodiment the SCFA is propionate and/or butyrate (i.e. propionate, butyrate or both).

Allergy can be prevented and/or treated in various ways. Increasing SCFA production represents a new clinical situation where they can be targeted in a new way.

So in a particular embodiment the prevention and/or treatment of allergy symptoms is obtained by increasing colonic acetate, propionate and/or butyrate production in said infant or young child.

In a particular embodiment the propionate and/or butyrate production is measured by Gas-Liquid Chromatography and it can be expressed in nmol/mg dry weight.

In a particular embodiment, the colonic butyrate production is increased by at least 10%, or at least 15% or at least 20% or at least 30% or at least 40% or at least 50% or at least 60% or at least 70% or at least 80% or at least 90% in comparison to the colonic butyrate production obtained with a nutritional composition without at least one N-acetylated oligosaccharide, at least one galacto-oligosaccharide and at least one sialylated oligosaccharide.

In a particular embodiment, the colonic butyrate production is increased by at least 10%, or at least 15% or at least 20% or at least 30% or at least 40% or at least 50% or at least 60% or at least 70% or at least 80% or at least 90% or at least 100% or more, in comparison to the colonic butyrate production obtained with a nutritional composition supplemented with common fibers like polydextrose or pectin.

In a particular embodiment, the colonic propionate production is increased by at least 10%, or at least 15% or at least 20% or at least 30% or at least 40% or at least 50% or at least 60% in comparison to the colonic propionate production obtained with a nutritional composition without at least one N-acetylated oligosaccharide, at least one galacto-oligosaccharide and at least one sialylated oligosaccharide.

In a particular embodiment, the colonic propionate production is increased by at least 10%, or at least 15% or at least 20% or at least 30% or at least 40% or at least 50% or at least 60% or at least 70% in comparison to the colonic propionate production obtained with a nutritional composition supplemented with common fibers like polydextrose or pectin.

Other Objects:

Another object of the present invention is the use of an oligosaccharide mixture comprising at least one N-acetylated oligosaccharide, at least one galacto-oligosaccharide and at least one sialylated oligosaccharide in the preparation of a nutritional composition for preventing and/or reducing allergy symptoms in an infant or a young child, by increasing SFCA, in particular colonic acetate, propionate and butyrate, production in said infant or young children, especially butyrate and/or propionate.

Another object of the present invention is the use of an oligosaccharide mixture comprising at least one N-acetylated oligosaccharide, at least one galacto-oligosaccharide and at least one sialylated oligosaccharide (or the use of a nutritional composition comprising such an oligosaccharide mixture) for increasing SCFA production, in particular colonic acetate, propionate and butyrate, in an infant or a young child, especially butyrate and/or propionate.

Another object of the present invention is the use of a nutritional composition comprising an oligosaccharide mixture that comprises at least one N-acetylated oligosaccharide, at least one galacto-oligosaccharide and at least one sialylated oligosaccharide for preventing and/or treating allergy symptoms in an infant or a young child, by increasing SFCA, in particular colonic acetate, propionate and butyrate, production in said infant or young children, especially butyrate and/or propionate.

Another object of the present invention is a pharmaceutical composition comprising an oligosaccharide mixture that comprises at least one N-acetylated oligosaccharide, at least one galacto-oligosaccharide and at least one sialylated oligosaccharide for use in preventing and/or reducing allergy symptoms in an infant or a young child, by increasing SFCA, in particular colonic acetate, propionate and butyrate, production in said infant or young children, especially butyrate and/or propionate.

Another object of the present invention is a method for preventing and/or treating allergy symptoms in an infant or a young child, by increasing SFCA production, in particular colonic acetate, propionate and butyrate, in said infant or young children, especially butyrate and/or propionate, said method comprising administering to said infant or young child a nutritional composition comprising an oligosaccharide mixture that comprises at least one N-acetylated oligosaccharide, at least one galacto-oligosaccharide and at least one sialylated oligosaccharide.

Another object of the present invention is a method for increasing SCFA, in particular colonic acetate, propionate and butyrate, production in an infant or a young child, especially butyrate and/or propionate, said method comprising administering to said infant or young child a nutritional composition comprising an oligosaccharide mixture that comprises at least one N-acetylated oligosaccharide, at least one galacto-oligosaccharide and at least one sialylated oligosaccharide.

Another object of the present invention is an oligosaccharide mixture comprising at least one N-acetylated oligosaccharide, at least one galacto-oligosaccharide and at least one sialylated oligosaccharide for use in a nutritional composition for an infant or a young child as a therapeutic agent that increases SCFA, in particular colonic acetate, propionate and butyrate, production in said infant or young child, especially butyrate and/or propionate.

Another object of the present invention is a nutritional composition comprising at least one N-acetylated oligosaccharide, at least one galacto-oligosaccharide and at least one sialylated oligosaccharide, for use as a therapeutic agent that increases SCFA production, in particular colonic acetate, propionate and butyrate, in an infant or a young child, especially butyrate and/or propionate.

The previously-mentioned embodiments and examples (e.g. related to the types and amounts of oligosaccharide, the nutritional composition, the administration, the targeted population . . . ) also apply for all these other objects.

EXAMPLES

The following examples illustrate some specific embodiments of the composition for use according to the present invention. The examples are given solely for the purpose of illustration and are not to be construed as limitations of the present invention, as many variations thereof are possible without departing from the spirit of the invention.

Example 1

An example of the composition of an infant formula comprising an oligosaccharide mixture according to the invention is given in the below table 1. The oligosaccharide mixture may for example comprise from 0.1 to 4.0 wt % of the N-acetylated oligosaccharide(s), from 92.0 to 99.5 wt % of the galacto-oligosaccharide(s) and from 0.3 to 4.0 wt % of the sialylated oligosaccharide(s).

TABLE 1 an example of the composition of a nutritional composition (e.g. an infant formula) according to the present invention

| Nutrients | per 100 kcal | per litre |
|---|---|---|
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (μg) | 8 | 50 |
| Se (μg) | 2 | 13 |
| Vitamin A (μg RE) | 105 | 700 |
| Vitamin D (μg) | 1.5 | 10 |
| Vitamin E (mg TE) | 0.8 | 5.4 |
| Vitamin K1 (μg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (μg) | 9 | 60 |
| Pantothenic acid (mg) | 0.45 | 3 |
| Vitamin B12 (μg) | 0.3 | 2 |
| Biotin (μg) | 2.2 | 15 |
| Choline (mg) | 10 | 67 |
| Fe (mg) | 1.2 | 8 |
| I (μg) | 15 | 100 |
| Cu (mg) | 0.06 | 0.4 |
| Zn (mg) | 0.75 | 5 |
| Oligosaccharide Mixture (g) | 1.38 | 9.0 |

Example 2

Description of the Study 5 week old females BALB/cByJ CRL mice from Charles River were split into several groups and fed during 6 weeks based on the following protocol:

Week 1: low-fiber diet (composition is detailed in table 2) for all groups

Weeks 2 to 6:

Control group (group A): low-fiber diet (same as for week 1)

Test groups (groups B-D): low-fiber diet (same as for week 1) supplemented with 5 wt % of a tested fiber (5% of the total low fiber diet was replaced by 5% of a tested fiber)

TABLE 2 composition of the low fiber diet

| Major Nutrients | |
|---|---|
| Dry matter | 93.9% |
| Crude protein | 18.0% |
| Crude fat | 5.0% |
| Crude fiber | 0.3% |
| Crude ash | 3.5% |
| Nitrogen-free extract (NFE) | 67.1% |
| Gross energy | 17.7 MJ/kg |
| Metabol. energy | 16.1 MJ/kg |
| Starch | 42.5% |
| Amino acids | |
| Arginine | 0.76% |
| Lysine | 1.66% |
| Methionine | 0.60% |
| Methionine + cystine | 0.97% |
| Tryptophan | 0.28% |
| Threonine | 0.92% |
| Major mineral elements | |
| Calcium | 0.62% |
| Phosphorus | 0.33% |
| Magnesium | 0.06% |
| Sodium | 0.24% |
| Potassium | 0.41% |
| Chlorine | 0.58% |
| Trace elements | |
| Iron | 50 mg/kg |
| Zinc | 37 mg/kg |
| Copper | 6 mg/kg |
| Iodine | 0.6 mg/kg |
| Manganese | 12 mg/kg |
| Selenium | 0.22 mg/kg |
| Vitamins added | |
| Vitamin A | 4'000 IE\|UI\|IU/kg |
| Vitamin D3 | 1'000 IE\|UI\|IU/kg |
| Vitamin E | 100 mg/kg |
| Vitamin K3 | 4 mg/kg |
| Vitamin B1 | 5 mg/kg |
| Vitamin B2 | 6 mg/kg |
| Vitamin B6 | 6 mg/kg |
| Vitamin B12 | 0.05 mg/kg |
| Nicotinic acid | 32 mg/kg |
| Pantothenic acid | 16 mg/kg |
| Folic acid | 2 mg/kg |
| Biotin | 0.2 mg/kg |
| Choline | 998 mg/kg |

The following fibers were tested:

BMOs=bovine milk oligosaccharides: an oligosaccharide mixture comprising 99.3% of GOS, 0.2% of N-acetylated oligosaccharide and 0.5% sialylated oligosaccharide was tested PDX=polydextrose Pectin Table 3 provides a summary of the different tested groups and diets.

TABLE 3 tested groups and diets of the study

| Group | Group label | Diet | Sample size |
|---|---|---|---|
| A | Pos ctr or Ctrl pos | Low-fiber diet | 8 |
| B | BMOs | Low-fiber diet + 5 wt % BMOs | 8 |
| C | PDX | Low-fiber diet + 5 wt % polydextrose | 8 |
| D | Pectin | Low-fiber diet + 5 wt % pectin | 8 |

After 6 weeks, the animals of each group were sacrificed and the content from caecum was collected. The SCFA production were measured by Gas-Liquid Chromatography (GLC; amounts of SCFA in nmol/mg dry weight). The following SCFA were measured: propionate, butyrate, valerate and acetate.

The measure was made based on the following protocol: SCFA in an acid solution (pH 2.0 to 3.0) were separated on a GLC column coated with a polar stationary phase. This allowed for minimal preparation of the sample (no derivatisation) and straightforward basic FID detection. SCFA were extracted from caecum using an acid phosphate buffer containing HgCl2 for inactivation of any residual bacterial activity and an internal standard (2,2 Dimethyl-butyric acid) for GLC analysis. After centrifugation, the sterile-filtered supernatant was ready for analysis by GLC. SCFA were measured simultaneously.

Median ratio values were calculated in order to compare the different fiber-enriched diets on SCFA production.

Findings

Figure 1:
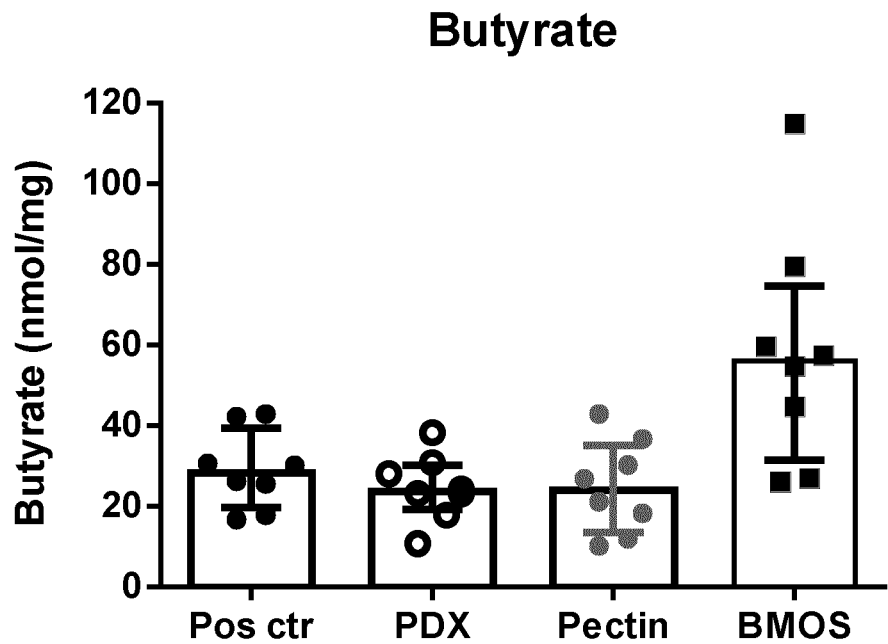
FIG. 1 represents the butyrate production from caecum of mice fed with low-fiber diets and with low-fiber diets enriched with 5% of different tested fibers.

The production of butyrate by BMOs enriched diet was significantly increased (see FIG. 1). Its production was increased by around 99% in comparison to the positive control. Its production was increased by 133% and by 136% in comparison to pectin and PDX, respectively.

The production of propionate by BMOs enriched diet was also significantly increased (see FIG. 2). Its production was increased by around 69% in comparison to the positive control. Its production was increased by 74% and by 75% in comparison to pectin and PDX, respectively.

These results are very surprising since pectin is usually seen as a high-inducer of SCFA (Stark et al, J Nutr. 1993, In vitro production of short-chain fatty acids by bacterial fermentation of dietary fiber compared with effects of those fibers on hepatic sterol synthesis in rats; Yang et al, Anaerobe, 2013, In vitro characterization of the impact of selected dietary fibers on fecal microbiota composition and short chain fatty acid production).

FIG. 3 represents the ratio of the median of each tested SCFA of each fiber-enriched diet divided by the median of the positive control diet (i.e. low-fiber diet only). A ratio of 1 (black line) means that there is no difference between the enriched diet and the control diet. A ratio below 1 means that the corresponding SCFA is higher in the control diet when compared to the fiber-enriched diet whereas a ratio above a means that the corresponding SCFA is higher with the fiber-enriched diet than the control. The PDX and Pectin enriched diets induced less SCFA release of all kinds. On the contrary the BMOS-enriched diet induces more SCFA release of all kinds (acetate, propionate, butyrate, valerate) as compared to the low-fiber diet as well as the other tested fibers. The BMOS-enriched diet was the only one to promote butyrate and propionate in such high amounts.

The inventors therefore surprisingly found that mice fed with a specific BMOs mixture were having a higher caecal (and therefore colonic) production for all the tested SCFA, and especially for butyrate and propionate.

Since SCFA, and especially butyrate and propionate, have been shown to protect against allergic airway disease and decrease allergic sensitization, a composition comprising an oligosaccharide mixture that comprises at least one N-acetylated oligosaccharide, at least one galacto-oligosaccharide and at least one sialylated oligosaccharide, would therefore be efficient in infants or young children for use in preventing and/or treating allergies and allergic symptoms later in life, by increasing colonic SCFA production in said infants or young children. Increasing colonic SFCA is therefore an attractive target to protect against allergy and allergic symptoms.

The invention claimed is:

1. A method for preventing and/or reducing allergy symptoms in an infant or a young child, by increasing short chain fatty acids (SCFA) production in the infant or young child, the method comprising administering a nutritional composition comprising an oligosaccharide mixture to the infant or young child,
   the oligosaccharide mixture comprising at least one N-acetylated oligosaccharide, at least one galacto-oligosaccharide and at least one sialylated oligosaccharide, and
   the nutritional composition has at least one formulation selected from the group consisting of (i) the at least one N-acetylated oligosaccharide comprises at least one of GalNAcβ1,3Galβ1,4Glc or Galβ1,6GalNAcβ1,4Glc; and (ii) the at least one sialylated oligosaccharide comprises at least one of NeuAcβ2,3Galβ1,4Glc or NeuAcβ2,6Galβ1,4Glc.

2. The method according to claim 1 wherein the reducing of the allergy symptoms comprises treating allergy symptoms in the infant or a young child, by increasing SCFA.

3. The method according to claim 1, wherein the at least one galacto-oligosaccharide is selected from the group consisting of Galβ1,3Galβ1,4Glc, Galβ1,6Galβ1,4Glc, Galβ1,3Galβ1,3Galβ1,4Glc, Galβ1,6Galβ1,6Galβ1,4Glc, Galβ1,3Galβ1,6Galβ1,4Glc, Galβ1,6Galβ1,3Galβ1,4Glc, Galβ1,6Galβ1,6Galβ1,6Glc, Galβ1,3Galβ1,3Glc, Galβ1,4Galβ1,4Glc, Galβ1,4Galβ1,4Galβ1,4Glc, and mixtures thereof.

4. The method according to claim 1, wherein the oligosaccharide mixture is present in an amount of from 2.5 to 15.0 wt % of the nutritional composition.

5. The method according to claim 1 comprising at least 0.01 wt % of the at least one N-acetylated oligosaccharide, at least 2.0 wt % of the at least one galacto-oligosaccharide and at least 0.02 wt % of at least one sialylated oligosaccharide.

6. The method according to claim 1, wherein the nutritional composition further comprises a prebiotic selected from the group consisting of human milk oligosaccharides, fructo-oligosaccharide, inulin, xylooligosaccharides, polydextrose and combinations thereof.

7. The method according to claim 1, wherein the nutritional composition further comprises a probiotic bacterial strain selected from the group consisting of *Lactobacillus acidophilus, Lactobacillus salivarius, Lactobacillus rhamnosus, Lactobacillus paracasei, Lactobacillus casei, Lactobacillus johnsonii, Lactobacillus plantarum, Lactobacillus fermentum, Lactobacillus lactis, Lactobacillus delbrueckii, Lactobacillus helveticus, Lactobacillus bulgari, Lactococcus lactis, Lactococcus diacetylactis, Lactococcus cremoris, Streptococcus salivarius, Streptococcus thermophilus, Bifidobacterium lactis, Bifidobacterium animalis, Bifidobacte-*

*rium longum, Bifidobacterium breve, Bifidobacterium infantis,* or *Bifidobacterium adolescentis* and mixtures thereof.

8. The method according to claim 1, wherein the nutritional composition is an infant formula.

9. The method according to claim 1, wherein the oligosaccharide mixture is derived from animal milk.

10. The method according to claim 1, wherein the SCFA is butyrate and/or propionate.

11. The method according to claim 10, wherein the oligosaccharide mixture is derived from one or more of cow's milk, goat's milk, buffalo's milk, or camel milk.

* * * * *